United States Patent [19]

Muchowski et al.

[11] 3,933,791

[45] Jan. 20, 1976

[54] OBTENTION OF DIGITOXIGENIN FROM NERIIFOLIN AND 2'-ACETYLNERIIFOLIN

[75] Inventors: Joseph M. Muchowski; Jose Iriarte, both of Mexico D. F., Mexico

[73] Assignee: Syntex (U.S.A.) Inc., Palo Alto, Calif.

[22] Filed: Sept. 16, 1974

[21] Appl. No.: 506,362

[52] U.S. Cl............................ 260/210.5; 424/182
[51] Int. Cl.².......................................... C07J 19/00
[58] Field of Search.................... 260/210.5, 239.57

[56] References Cited
UNITED STATES PATENTS 2,752,372  6/1956  Reichstein ...................... 260/210.5

3,682,891  8/1972  Radscheit et al. ............. 260/239.57

OTHER PUBLICATIONS

Fieser and Fieser, *Reagents for Organic Syn.*, Wiley and Sons, Inc. 1967, p. 146.
Wagner and Zook, Synthetic Org. Chemistry, Wiley and Sons, Inc., New York, 1953, pp. 34–35.

*Primary Examiner*—Lewis Gotts
*Assistant Examiner*—Cary Owens
*Attorney, Agent, or Firm*—Gerard A. Blaufarb; William B. Walker

[57] ABSTRACT

Process for degrading the glycoside neriifolin and its acetate to the cardenolide digitoxigenin. Novel intermediates are also described.

9 Claims, No Drawings

OBTENTION OF DIGITOXIGENIN FROM NERIIFOLIN AND 2'-ACETYLNERIIFOLIN

The present invention is directed to a process for obtaining digitoxigenin from the monoglycosides heriifolin and 2'-acetylneriifolin and to certain novel intermediates obtained thereby.

Digitoxigenin is a typical and widely distributed cardenolide aglycone which possesses much of the cardiac activity of the glycosides from which it is derived.

It is known that thevetin and other related glycosides such as neriifolin contained in the seeds of *Thevetia neriifolia Juss* (Apocinaceae) are derivatives of the 5β,14β-cardenolide digitoxigenin [see for example H. Helfenberger and T. Reichstein, *Helv. Chim. Acta* 31, p. 1470 and p. 2097 (1948) and M. Frerejacque, *Compt. rend.* 221, p. 645 (1945), *Compt. rend.* 225, p. 695 (1947) and Compt. rend. 242, 2395 (1956)]. However, this aglycone was never actually isolated by degradation of the glycosides, whose chemical structures were proved by indirect evidence. Thus, the first attempts made by Helfenberger and Reichstein (*Helv. Chem. Acta* 31, 1470 (1948) to cleave neriifolin to the aglycone by acid treatment afforded only an small amount of "β"-anhydro digitoxigenin, recovering most of the starting glycoside. These authors described later [*H. Chem. Acta* 31, 2097 (1948)], the oxidation of neriifolin with chromium trioxide in acetic acid followed by successive acid and alkaline treatments and a second $CrO_3$ oxidation, obtaining digitoxigenone in very low yields; they also degraded neriifolin to 3β-acetoxy etiocholanic acid methyl ester, however they were unable to obtain digitoxigenin in pure form.

Other species of Thevetia, e.g. *Thevetia Thevetoides* (H.B.K.) Schum: contain thevetin and 2'-acetyl-thevetin.

Thevetin is a triglycoside in which digitoxigenin is linked to a 2,4-dihydroxy-3-methoxy-5-methyl sugar, thevetose, and through this, to two glucose units. Enzymatic hydrolysis of thevetin and 2'-acetylthevetin by means of the enzymes contained in the same seeds affords the α-L-monoglycosides neriifolin and 2'-acetylneriifolin represented by the formula:

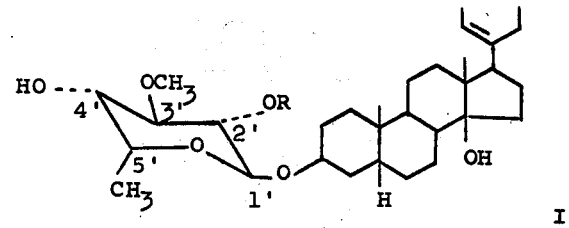

wherein R is hydrogen or acetyl.

The cleavage of the thevetose unit in these compounds, to yield the cardenolide digitoxigenin has been unsuccessful up to date either by enzymatic or chemical means.

In accordance with the present invention we have discovered a method for degrading the monoglycosides neriifolin and its acetate, either the individual compounds or as a mixture of glycosides, to digitoxigenin in surprisingly high yields.

This method can be illustrated by the following sequence of reactions:

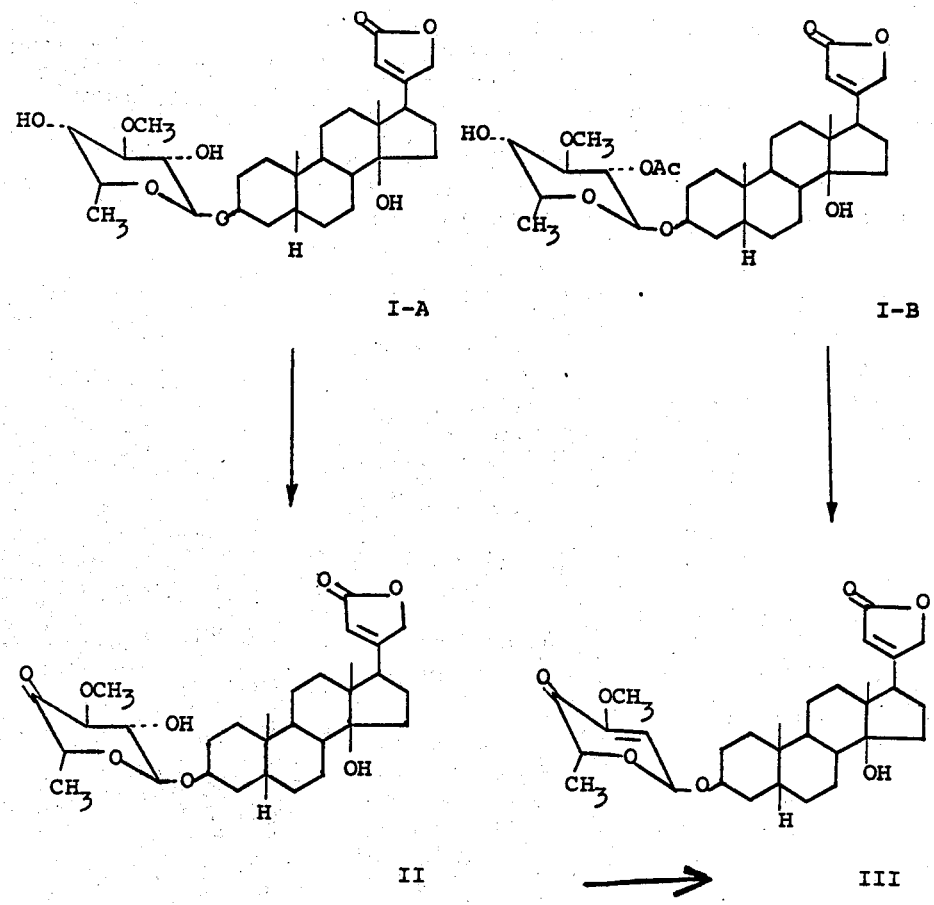

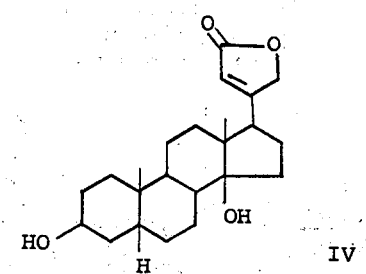

wherein Ac is acetyl.

In practicing the process illustrated above, neriifolin (I-A) is oxidized with chromium trioxide, using particularly chromium trioxide-dipyridine complex, to produce the 4'-keto derivative of neriifolin of formula II. This reaction is effected under anhydrous conditions using from 4 to 10 molar equivalents of the reagent per molar equivalent of starting compound, preferably about 6 molar equivalents, in methylene chloride solution, or using a methylene chloridepyridine mixture as solvent, at a temperature comprised between -5°C to room temperature for a period of time of the order of about 15 to 45 minutes. The reagent can be prepared in situ or previously prepared. The crude product can be purified by chromatographic techniques, to yield pure compound II, however, this is not necessary.

Upon reaction of the crude oxidation product, containing the 4'-keto derivative of neriifolin (II) with acetic anhydride in pyridine solution in a conventional manner, there is obtained the α,β-unsaturated ketone of formula III. The conditions used for this dehydration reaction are not critical, thus the reaction can be conducted at temperatures comprised between 0°C to reflux, for a period of time of between 2 to 20 hours. In the preferred embodiments, the reaction is conducted at about room temperature or under slight heating (about 40°C) for about 3 to 16 hours.

The crude α,β-unsaturated ketone (III) is then treated with dilute sulfuric acid in methanol solution, using particularly an about 0.05N aqueous methanolic sulfuric acid solution, at reflux temperature for a period of time of about 30-35 minutes to yield digitoxigenin (IV) in yields of the order of 40-50 percent. Longer reaction times diminish the yields of digitoxigenin.

When 2'-acetylneriifolin (I-B) is oxidized with chromium trioxide-dipyridine, complex, as described hereinbefore in detail with regard to the oxidation of free neriifolin, there is obtained the α,β-unsaturated ketone III in a straightforward manner, which upon hydrolysis with sulfuric acid in aqueous methanol affords digitoxigenin (IV) in about 65-70 percent yield.

Alternatively, the above-described process can be carried out starting from a mixture of neriifolin and 2'-acetylneriifolin. Thus, a mixture of I-A and I-B is oxidized with chromium trioxide-dipyridine complex to a mixture which contains compounds of formulas II and III, dehydrated with acetic anhydride in pyridine and hydrolyzed with aqueous methanolic sulfuric acid to digitoxigenin. In this case the yields of digitoxigenin depend on the proportion in which neriifolin and its acetate are present in the mixture used as starting material. However, better yields are obtained when using the pure individual glycosides.

In a further aspect, and in spite of the discouraging results obtained by Helfenberger and Reichstein (vide supra) we found that when neriifolin (I-A) is oxidized with an excess of chromium trioxide in acetic acid for a prolonged period of time, of the order of 20 to 30 hours followed by treatment with sulfuric acid in aqueous methanol, as previously described, there is obtained digitoxigenin (IV) in about 22–32 percent yield.

The glycosides neriifolin and its acetate used as starting materials have been obtained from the seeds of *Thevetia thevetoides* (H.B.K.) Schum:. Typically, the glycosides are isolated as follows:

The powder obtained after peeling, grinding and defatting the seeds, which contains thevetin and 2'-acetylthevetin, is subjected to hydrolytic cleavage by the action of the enzymes present within this material, incubating its aqueous suspension at 37°–40°C, optionally in the presence of a small amount of toluene, for a prolonged period of time, i.e., for about 6 days. The insoluble material is eliminated and the glycosides are isolated from the solution by extraction with chloroform and chloroform-methanol, and purified by crystallization to obtain the pure neriifolin in about 4 percent yield and 2'-acetylneriifolin in about 1–1.5 percent yield. When the organic extracts are evaporated to dryness there is obtained a mixture of neriifolin and its acetate about 70 percent pure, as demonstrated by thin layer chromatographic analysis.

It is obvious that other plant sources of these glycosides can also be practical.

The following Examples illustrate the invention but are not intended to limit its scope.

PREPARATION

Three kilograms of peeled, finely grounded seeds of *Thevetia thevetoides* (H.B.K.) Schum: is defatted with 9 l. of hexane. The solid residue (1.058 kg) is suspended 8 l. of water and 60 ml. of toluene, and the resulting mixture is incubated at 37°–40°C for 6 days. The insoluble material is separated by filtration through Celite, diatomaceous earth, and washed with approximately 10 l. of methanol. The combined filtrates are concentrated to one-third its original volume and extracted several times with chloroform. The extracts are washed with water and the combined aqueous phases reextracted with chloroform-methanol (9:1). The combined organic extracts are dried over sodium sulfate and evaporated to dryness under reduced pressure. Crystallization of the residue from methanol-water affords 25 g. of neriifolin, m.p. 209°–214°C; $[\alpha]_D$ −49°(MeOH) λmax 218 nm (ε17,300). The mother liquors are chromatographed on silica gel to yield 9 g. of 2'-acetylneriifolin which is further purified by crystallization from methanol-water, m.p. 218°–220°C; $[\alpha]_D$ − 91°(CHCl₃); λmax 218 nm (ε23,050). These compounds are identical to authentic samples of neriifolin and 2'-acetylneriifolin, respectively.

The above procedure is repeated starting from 430 g. of seeds, omitting the final separation of the monoglycosides by crystallization, thus obtaining 12.95 g. of the mixture of neriifolin and its acetate as a yellow foam.

EXAMPLE 1

To a mixture of 30 g. of anhydrous pyridine and 75 ml. of anhydrous methylene chloride (distilled over phosphorous pentoxide) are added 3 g. of chromium trioxide, stirring the reaction mixture at room temperature for 15 minutes. The chromium trioxide-dipyridine complex thus obtained is then cooled to about $-10°$ to $-5°C$ and a solution of 3 g. of 2'-acetylneriifolin is added, stirring the reaction mixture for 15 minutes at the same temperature. The insoluble material is separated by filtration through Celite, diatomaceous earth, washing the solids with chloroform. The combined organic filtrates are evaporated to dryness under reduced pressure at low temperature, the solid residue is then dissolved in methylene chloride and filtered through a silica gel column (60 g.) to eliminate the chromium salts. After evaporation of the solvent there are obtained 840mg. of the crude 2'-deoxy-2'-dehydro-4'-keto derivative of neriifolin of the formula:

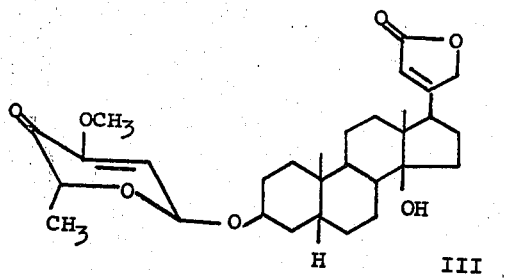

which can be further purified by crystallization from methanol-water, [m.p. 119°–123°C; $[\alpha]_D$ $-51.46°(CHCl_3)$; $\lambda$max 218 nm ($\epsilon$15,000); ir 3540, 3460, 1780, 1740, 1640 cm$^{-1}$; 100 Mc nmr: 0.87 (18-H), 0.94 (19 -H), 1.37 (d. J7 Hz, 5'-Me); 2.75 (m, 17$\alpha$-H), 3.63 (CH$_3$O), 4.03 (3$\alpha$-H), 4.58 (m, J7Hz, 5'-H), 4.75 (dd, J, 18 Hz, J$_2$ 2Hz, 21-H), 5.00 (dd, J, 18 Hz, J$_2$ 2Hz, 21-H), 5.41 (d, J 4 Hz, 1'-H), 5.68 (d, J 4Hz, 2'H), 5.85 ppm (22-H); MS 514 (M$^+$), (M—C$_7$H$_9$O$_3$), 339 (M—C$_7$H$_9$ O$_3$—H$_2$O), 141 (M-357) ].

To a solution of 420 mg. of the foregoing intermediate in 25 ml. of methanol are added 20 ml. of 0.1N sulfuric acid, and the reaction mixture is heated at reflux temperature for 30 minutes, cooled and concentrated under reduced pressure at about 25°C until precipitation. It is then diluted with ice-water, and the solid material filtered off, washed with water, sodium bicarbonate solution and water, and air dried, thus obtaining 116 mg. of crude digitoxigenin, m.p. 218°–223°C, which can be further purified by recrystallized from methanol-water to yield the pure compound, [m.p. 244-6°C; $[\alpha]_D$ +19.3°(CHCl$_3$); $\lambda$max 218 nm ($\epsilon$14,130); ir 3520, 3450, 1780, 1730, 1625 cm$^{-1}$; nmr 0.85 (18-H), 0.93 (19 -H), 2.70 (m 17$\alpha$-H), 4.07 (3$\alpha$-H), 4.67 (dd J, 18 Hz, J$_2$2 Hz, 21-H), 5.00 (dd J, 18 Hz, J$_2$ 2 Hz, 21-H)], 5.78 ppm (22-H), identical to an authentic sample of digitoxigenin.

EXAMPLE 2

To a mixture of 60 g. of anhydrous pyridine and 75 ml. of anhydrous methylene chloride are added 6 g. of chromium trioxide, and the resulting mixture is stirred at room temperature for 15 minutes, it is cooled to $-10°$ to $-5°C$ and a solution of 3 g. of 2'-acetylneriifolin in 30 ml. of methylene chloride is added, stirring the reaction mixture at the same temperature for 15 minutes and thereafter at 10°C for 30 minutes further. The solid material is separated by filtration and the filtrate evaporated to dryness under vacuo at low temperature. The residue is dissolved in methylene chloride, filtered through 60 g. of silica gel, and the organic solution evaporated to dryness under vacuo. The residue is dissolved in 175 ml. of methanol, 150 ml. of 0.1N sulfuric acid is added and the mixture is refluxed for 30 minutes, cooled, concentrated to a small volume under reduced pressure at low temperature, until a precipitate is formed, diluted with ice-water and the solid material filtered off, thus obtaining 1.29 g. of crude digitoxigenin. Recrystallization from acetone-ether affords the pure cardenolide, [m.p. 246°–249°C; $[\alpha]_D$ +22°(MeOH); $\lambda$max 217 nm ($\epsilon$15,500)], identical to an authentic sample.

EXAMPLE 3

To a suspension of 11.5 g. of Celite, diatomaceous earth, (dried at 125°C for 20 hours) in 250 ml. of anhydrous methylene chloride, cooled to $-5°$ to $0°C$ is added 5.83 g. of chromium trioxide-dipyridine complex [J. C. Collins et al., Tetrahedron Letters 30,3363- 3366 (1968)]. To the stirred mixture are added 1.5 g. of neriifolin dissolved in 80 ml. of methylene chloride, and the resulting mixture is stirred at said temperature for 15 minutes, 11.5 g. of sodium bisulfate hydrate are added and the reaction mixture stirred for 10 additional minutes. The solid material is separated by filtration and washed with methylene chloride. The combined filtrates are evaporated to dryness under reduced pressure, at low temperature to yield a crude material containing the 4'-keto derivative of neriifolin, which can be purified by thin layer chromatography using ethyl acetate-hexane (70:30) as eluant, thus obtaining the pure compound represented by the formula:

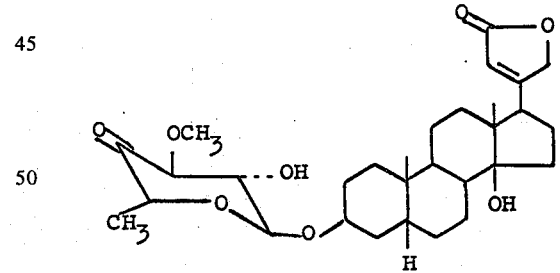

which is further purified by crystallization from methanol-water. This compound has the following constants: m.p. 163°–166°C; $[\alpha]_D$ $-84°$(MeOH); $\lambda$max 216 nm ($\epsilon$13,500); ir 3400, 1780, 1740, 1620 cm$^{-1}$ 100 MC nmr: 0.88 (18-H), 0.97 (19-H), 3.60 (CH$_3$O—),

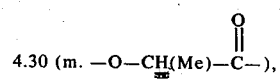

4.30 (m. —O—CH(Me)—C—), 4.74 (dd J, 18 Hz, J$_2$ 2Hz, 21-H), 4.99 (dd J, 18 Hz, J$_2$ 2Hz, 21-H), 5.84 ppm (22-H); Calcd. for C$_{30}$H$_{44}$O$_8$: C, 67.64; H, 8.33. Found: C, 66.86; H, 8.43; MS 533 (M$^+$+H), 357 (M-C$_7$H$_{11}$O$_4$—H$_2$O).

EXAMPLE 4

A solution of 500 mg. of the crude material containing the 4'-keto derivative of neriifolin, in 15 ml. of pyridine is treated with 5 ml. of acetic anhydride and the reaction mixture is allowed to stand at room temperature for 3 hours, poured into ice-water containing 150 mg. of sodium acetate and extracted several times with chloroform. The combined organic extracts are washed with water, dried over sodium sulfate and evaporated to dryness. The residue is purified by t.l.c. to afford the pure 2'-deoxy-2'-dehydro-4'-keto derivative of neriifolin, m.p. 119°–123°C, identical to the compound obtained in Example 1.

EXAMPLE 5

To a suspension of 46 g. of Celite (diatomaceous earth), dried for 20 hours at 125°C. in 100 ml. of anhydrous methylene chloride cooled to −5°to 0°C is added 36 g. of chromium trioxide-dipyridine complex. A solution of 6 g. of neriifolin in 320 ml. of methylene chloride containing 5% pyridine is added and the reaction mixture is stirred for 25 minutes at room temperature. It is then filtered through silica gel and the filtrate is stirred with 30 g. of sodium bisulfate hydrate for 20 minutes, the solid is separated by filtration and the filtrate is evaporated to dryness under vacuo. The residue is submitted to thin layer chromatography using ethyl acetane-hexane (70:30) as eluant, to obtain 3.3 g. of a crude material containing the 4'-keto derivative of neriifolin and 1.8 g. of recovered neriifolin.

To a solution of 3.3 g. of the crude material containing the 4'-keto derivative of neriifolin in 33 ml. of anhydrous pyridine is added 9.5 ml. of acetic anhydride and the reaction mixture is heated at 40°C for 16 hours. It is then poured into ice-water, 5 g. of sodium acetate are added and then most of the solvent eliminated under vacuo. The residue is extracted with methylene chloride, and the organic extract washed with water, 0.1N sulfuric acid and water to neutrality, dried over magnesium sulfate and evaporated to dryness, to give 3.26 g. of the crude 2'-deoxy-2'-dehydro-4'-keto derivative of neriifolin, which is dissolved in 190 ml. of methanol, 155 ml. of 0.1N sulfuric acid is added and the reaction mixture is refluxed for 30 minutes and then concentrated under vacuo to a small volume. The solid which forms is extracted with methylene chloride, and the combined organic extracts washed with water, sodium carbonate solution and water to neutrality, dried over magnesium sulfate and evaporated to dryness under vacuo. The residue is purified by chromatography on silica gel plates using ethyl acetate-hexane (70:30) as gradient, to obtain 1.3 g. of digitoxigenin, which can be further purified by crystallization from methanol-water.

EXAMPLE 6

To a suspension of 23 g. of dried Celite, diatomaceous earth in 500 ml. of anhydrous methylene chloride are added 15 g. of chromium trioxide-dipyridine complex, the mixture is stirred for 10 minutes and thereafter a solution of 2.5 g. of a crude mixture of neriifolin and 2'-acetylneriifolin (containing about 55% of neriifolin and 15% of its acetate) is added. The reaction mixture is stirred for 15 minutes at room temperature; the insoluble material is separated by filtration and washed with ethyl acetate. The combined organic extracts are filtered through a column of silica gel (50 g.) washing the column with ethyl acetate, and the combined eluates are evaporated to dryness, to yield 2.3 g. of a crude product containing the 4'-keto and 2'-deoxy-2'-dehydro-4'-keto derivatives of neriifolin. The crude reaction product is dissolved in 25 ml. of pyridine, 6.7 ml. of acetic anhydride are added and the mixture is heated at 40°C for 2 hours, poured into ice water and extracted with ethyl acetate. The organic extract is washed with 6N hydrochloric acid solution and water to neutrality, dried over magnesium sulfate and evaporated to dryness under vacuo. The residue (2.2 g.) is dissolved in 235 ml. of a 0.05N solution of sulfuric acid in methanol-water (1:1), refluxing the reaction mixture for 30 minutes. It is then cooled, neutralized with sodium bicarbonate solution, concentrated to half volume under vacuo and extracted with methylene chloride. The organic extract is washed with water, dried over magnesium sulfate and evaporated to dryness under vacuo. Purification of the residue by chromatography on silica gel, using ethyl acetatehexane (70:30) as eluant affords 498 mg. of digitoxigenin.

EXAMPLE 7

To a stirred solution of 2.4 g. of neriifolin in 30 ml. of glacial acetic acid is added dropwise a solution of 2.88 g. of chromium trioxide in 175 ml. of glacial acetic acid, and the reaction mixture is stirred for 22 hours at room temperature. It is then poured into ice-water and extracted with chloroform. The organic extracts are washed with saturated sodium bisulfite solution and water to neutrality, dried over sodium sulfate and evaporated to dryness under vacuo, at low temperature. The crude residue (1.89g.) is dissolved in 120 ml. of methanol, 91 ml. of 0.1N sulfuric acid are added and the reaction mixture is refluxed for 30 minutes, cooled and concentrated under vacuo to a small volume. The formed precipitate is separated by filtration and purified by thin layer chromatography using hexane-ethyl acetate (70:30) as eluant, thus obtaining 520 mg. of pure digitoxigenin m.p. 240°–243°C, identical to an authentical sample.

What is claimed is:

1. A process for obtaining digitoxigenin which consists essentially of hydrolyzing a compound of the formula:

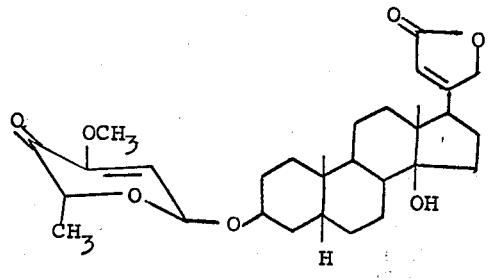

with dilute sulfuric acid in methanol solution and separating the digitoxigenin thus obtained.

2. The process of claim 1 in which there is used a 0.05N solution of sulfuric acid in aqueous methanol (1:1), conducting the reaction at reflux temperature for about 30 minutes.

3. The process of claim 1 including the previous steps of oxidizing neriifolin with chromium trioxidedipyridine complex and dehydrating the oxidation product with acetic anhydride in pyridine.

4. The process of claim 3 in which there are used about 6 molar equivalents of chromium trioxide-dipyridine complex per molar equivalent of neriifolin.

5. The process of claim 1 including the previous step of oxidizing 2'-acetyl neriifolin with chromium trioxide-dipyridine complex.

6. The process of claim 5 in which there are used about 6 molar equivalents of chromium trioxide-dipyridine complex per molar equivalent of 2'-acetylneriifolin.

7. The process of claim 1 including the previous steps of oxidizing a mixture of neriifolin and 2'-acetylneriifolin with chromium trioxide-dipyridine complex, and dehydrating the oxidation product with acetic anhydride in pyridine.

8. A compound of the formula:

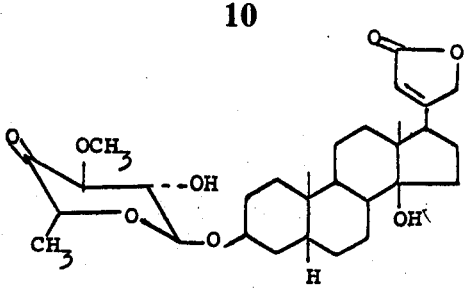

9. A compound of the formula:

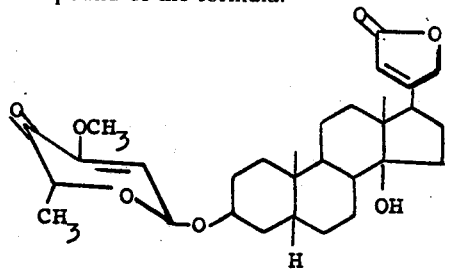

* * * * *